United States Patent
Yamaguchi et al.

(10) Patent No.: US 9,113,981 B2
(45) Date of Patent: Aug. 25, 2015

(54) EJECTION DEVICE AND METHOD OF FILLING THE EJECTION DEVICE WITH A MATERIAL

(75) Inventors: Nobutoshi Yamaguchi, Tokyo (JP); Hironobu Akizumi, Tokyo (JP); Yusaku Andoh, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 400 days.

(21) Appl. No.: 13/641,927

(22) PCT Filed: Apr. 20, 2011

(86) PCT No.: PCT/JP2011/059743
§ 371 (c)(1),
(2), (4) Date: Oct. 18, 2012

(87) PCT Pub. No.: WO2011/132714
PCT Pub. Date: Oct. 27, 2011

(65) Prior Publication Data
US 2013/0032241 A1 Feb. 7, 2013

(30) Foreign Application Priority Data

Apr. 22, 2010 (JP) .................. 2010-099145
Mar. 8, 2011 (JP) .................. 2011-050786

(51) Int. Cl.
*A61C 5/04* (2006.01)
*A61C 5/06* (2006.01)

(52) U.S. Cl.
CPC . *A61C 5/062* (2013.01); *A61C 5/04* (2013.01); *A61C 5/064* (2013.01)

(58) Field of Classification Search
CPC ....... A61M 5/1782; A61C 5/04; A61C 5/062; A61C 5/064

USPC .............. 141/2, 20, 27, 319; 433/89
See application file for complete search history.

(56) References Cited

U.S. PATENT DOCUMENTS 3,724,076 A 4/1973 Schmitz
3,729,031 A * 4/1973 Baldwin .................. 141/2
(Continued)

FOREIGN PATENT DOCUMENTS

JP 2001-346812 12/2001
JP 2002-191621 7/2002
(Continued)

OTHER PUBLICATIONS

Japanese Office Action dated Oct. 28, 2014 issued in the corresponding Japanese patent application No. 2012-511689.

*Primary Examiner* — Timothy L Maust
(74) *Attorney, Agent, or Firm* — Rankin, Hill & Clark LLP

(57) ABSTRACT

[Problems] To fill a container with a material without applying a high pressure to the material that is to be filled.
[Means for Solution] An ejection device 1 comprises a filling chamber 24 formed in a cylindrical member for containing a material to be filled, a discharge portion 7 having a discharge nozzle 12 for pouring out the filled material to the exterior, and a piston 4 that pushes the filled material toward the front end side of the filling chamber 24 to discharge the filled material through the discharge nozzle 12. In the ejection device 1, the discharge portion 7 is formed separately from the filling chamber 24 and in a manner to be fitted to an opening on one end side of the cylindrical member 24, the opening serving as a filling port for filling the material to be filled, and after the material to be filled is poured into the filling chamber 24 through the filling port, the discharge portion 7 is coupled to the filling chamber 24.

11 Claims, 8 Drawing Sheets

(56) References Cited

U.S. PATENT DOCUMENTS

| | | | |
|---|---|---|---|
| 4,243,080 A * | 1/1981 | Choksi et al. | 141/2 |
| 4,569,662 A * | 2/1986 | Dragan | 433/89 |
| 5,566,729 A * | 10/1996 | Grabenkort et al. | 141/25 |
| 6,425,420 B2 * | 7/2002 | Both et al. | 141/2 |
| 6,684,918 B1 * | 2/2004 | Thilly et al. | 141/25 |
| 6,755,220 B2 * | 6/2004 | Castellano et al. | 141/27 |
| 6,848,480 B2 * | 2/2005 | Brennan | 141/2 |
| 6,901,975 B2 * | 6/2005 | Aramata et al. | 141/319 |
| 7,963,937 B2 * | 6/2011 | Pauser et al. | 604/82 |
| 2002/0068257 A1 | 6/2002 | Albach | |
| 2002/0098462 A1 * | 7/2002 | Kaneko et al. | 433/89 |
| 2008/0203112 A1 * | 8/2008 | Peuker et al. | 222/137 |

FOREIGN PATENT DOCUMENTS

| | | |
|---|---|---|
| JP | 2002-219138 | 8/2002 |
| JP | 2008-501494 | 1/2008 |
| JP | 2009-112473 | 5/2009 |
| WO | 2009/021033 | 2/2009 |

\* cited by examiner

EJECTION DEVICE AND METHOD OF FILLING THE EJECTION DEVICE WITH A MATERIAL

TECHNICAL FIELD

This invention relates to an ejection device which enables a container to be filled with a viscous material or enables a container having a nozzle of a small diameter to be filled with a viscous material without applying a high pressure, and to a method of filling the ejection device with the material.

BACKGROUND ART

A patent document 1 described below is disclosing a disposable container filled with a material for dental treatment. On other words, the disposable container is filled with the material for dental treatment in an amount sufficient for the use of one time and is, usually, discarded after the use of one time. The container is provided with a cylindrical body portion, and has a nozzle formed at a front end of the body portion and a piston contained in the body portion. Before the material is being filled, the piston is disposed on the front end side of the body portion, i.e., is disposed on the nozzle side.

To pour the material into the disposable container, use is made of a stock container which contains the material. The stock container is provided with a port in which the nozzle of the disposable container is to be inserted, and the nozzle of the disposable container is set into a push-in port. To pour the material into the disposable container, the material contained in the stock container is pressurized and is poured into the disposable container through the nozzle and, at the same time, the piston in the container moves back being pushed by the material that is poured. After the piston is moved back to a predetermined position, the pouring is discontinued and the disposable container is thus filled with the material.

At the start of pouring the material that is to be filled, the piston is disposed at the front end of the body portion of the disposable container so that no air remains in the container.

In other words, if the material is poured from the rear end side of the body portion, the materials flows from the opening on the rear end side toward the filling surface on the front end side inevitably trapping the air on the way of flowing through the body portion and flowing into the filling surface. On the other hand, by disposing the piston at the front end position of the body portion of the disposable container, pouring the material into the container through the nozzle, maintaining the filling surface in close contact with the front end surface of the piston, and moving the piston back in proportion to an increase in the amount of filling, it is allowed to greatly decrease the amount of the air that remains in the material that is filled. Thus, upon eliminating the air that remains and discontinuing the pouring of the material at a predetermined position to where the piston has moved back, it is allowed to pour the material in a correct amount.

PRIOR ART DOCUMENT

Patent Document

Patent document 1: JP-A-2001-346812

OUTLINE OF THE INVENTION

Problems that the Invention is to Solve

If it is attempted to fill the container of a diameter of about 5 mm with a viscous material by letting it to naturally flow down, a pressure of a certain degree must be applied thereto because of the viscosity.

The disposable container has the nozzle of a small diameter through which the material is poured. According to the pouring method of the patent document 1, therefore, a high pressure of about 100 to about 300 N is applied at the time of pouring a highly viscous material such as a material for dental use. Further, being compounded by the load of when the material moves the piston 4 back, there occur a phenomenon in that the material separates into liquid components (monomers) and solid components (filler and the like) as well as a problem of curing, causing deterioration in the quality of the material filled therein.

At the start of pouring the material as described above, the piston is disposed at the front end position of the body portion of the disposable container so that no air remains in the container.

To release the air, the inner periphery surface of the container and the outer periphery surface of the piston may be loosely fitted together. If fitted too loosely, however, the material filled therein may often leak together with the air. If the inner periphery surface of the container and the outer periphery surface of the piston are tightly fitted together, then the air cannot be released.

For the lowly viscous materials, on the other hand, if it is attempted to release the air through between the piston and the inner periphery surface of the container at the time of pouring the material, the material that is filled leaks together with the air. If there is no gap between the piston and the inner periphery surface of the container, the air is entrapped in the material that is filled and turns into air bubbles due to the pressure of pouring, and the air bubbles often remain therein. On other words, with the lowly viscous material, it is difficult to release the air only without forming air bubbles. In either case, the relatively expensive material for dental use was so far wasted.

The present invention was accomplished in view of the above-mentioned circumstances, and has an object of providing an ejection device that enables the container to be filled with the material without applying a high pressure and a method of filling the ejector device with the material.

Means for Solving the Problems

To achieve the above object, an ejection device of the invention comprises a filling chamber formed in a cylindrical member for containing a material to be filled, a discharge portion having a discharge nozzle for pouring out the filled material to the exterior, and a piston that pushes the filled material toward the front end side of the filling chamber to discharge the filled material through the discharge nozzle; wherein the discharge portion is formed separately from the filling chamber and in a manner to be fitted to an opening on one end side of the cylindrical member, the opening serving as a filling port for filling the material to be filled; and after the material to be filled is poured into the filling chamber through the filling port, the discharge portion is coupled to the opening of the cylindrical member.

In the above ejection device, the discharge portion is formed integrally with a main body that removably contains the filling chamber therein, the filling chamber is contained in the main body, and the discharge portion is coupled to the filling port.

In the above ejection device, the filling chamber is made of an elastic member so that the volume of the filling chamber elastically increases when the piston is pushed, a gap is formed between the main body and the filling chamber, and the volume of the filling chamber decreases when the piston is no longer pushed.

In order to achieve the above object, a method of filling an ejection device with a material according to the invention is a method of filling a filling chamber of an ejection device with a material that is introduced with pressure from a stock container filled with the material through an extrusion port formed in the stock container, comprising a step of setting the extrusion port by connecting the opening on one end side of the filling chamber to the extrusion port of the stock container, and setting the piston on the side of the opening; a step of pressurizing the material filled in the stock container; a step of filling the filling chamber with the material while pushing the piston backward by the material extruded through the extrusion port in the pressurizing step; and a step of coupling the discharge portion equipped with a nozzle for pouring out the material to the opening on one end side of the filling chamber after the filling chamber has been filled with the material.

In the ejection device, a groove is formed in the inner periphery surface of the cylindrical member, the groove being formed from the other end side of the cylindrical member up to the interior of the filing chamber with the piston at its retreated position.

In the ejection device, a step is formed in the inner periphery surface of the cylindrical member being corresponded to an end portion of the groove on the side of the filling chamber, the portion from the step to the opening on one end side of the filling chamber being a contracted inner diameter portion in which the piston is inserted in a tightly fitted state, and a portion from the step to the opening on the other end side of the filling chamber being an expanded inner diameter portion in which the piston is inserted in a loosely fitted state.

In order to achieve the above object, a method of filling an ejection device with a material according to the invention is a method of filling a filling chamber of an ejection device with a material that is introduced with pressure from a stock container filled with the material through an extrusion port formed in the stock container, comprising a step of setting the extrusion port by connecting the opening on one end side of the filling chamber to the extrusion port of the stock container, and setting the piston at its retreated position; a step of pressurizing the material filled in the stock container; a step of filling the filling chamber with the material while releasing the air in the filling chamber through the groove formed in the inner periphery surface of the cylindrical member in the pressurizing step; and a step of coupling the discharge portion equipped with a nozzle for pouring out the material to the opening on one end side of the filling chamber after the filling chamber has been filled with the material.

In the method of filling the ejection device with the material, when the ejection device has a step formed in the inner periphery surface of the cylindrical portion, the filling chamber can be filled with the material in the step of filling while also releasing the air in the filling chamber through a gap between the inner periphery surface of the cylindrical portion in the expanded diameter portion of the cylindrical member and the outer periphery surface of the piston.

Effects of the Invention

In the ejection device of the invention, the discharge portion is formed separately from the filling chamber and in a manner to be fitted to an opening on one end side of the filling chamber, the opening serving as a filling port for filling the material to be filled, and after the material to be filled is poured into the filling chamber through the filling port, the discharge portion is coupled to the filling chamber. Thus, the material to be filled is poured through the opening of the filling chamber, and no high pressure is applied to the material that is being poured into the filling chamber. Therefore, the material that is filled is prevented from separating into liquid components and solid components, or from being cured. Specifically, the conventional devices that are using a discharge portion having a nozzle of a small diameter are now liberated from the need of filling the material through the nozzle, which is a distinguished effect.

Further, the filling chamber is made of an elastic member so that the volume of the filling chamber elastically increases when the piston is pushed, a gap is formed between the main body and the filling chamber, and the volume of the filling chamber decreases when the piston is no longer pushed. Therefore, the material that is filled is prevented from adhering on the nozzle of the discharge portion.

Upon forming a groove or a step in the cylindrical container, further, the ejection device can be easily formed to meet the viscosity of the material that is filled. This is effective in releasing the air from the filling chamber or in preventing the leakage of the filled material particularly for the lowly viscous materials that are filled. Since no pressure is applied to the material that is filled, air bubbles are prevented from being mixed, too.

MODES FOR CARRYING OUT THE INVENTION

The ejection device according to a first embodiment of the invention and a method of filling the ejection device with a material will now be described with reference to the drawings. In this specification, the side on where an end of the nozzle is present is referred to as the front end (front) side and the opposite side is referred to as the rear end (rear) side.

Figure 1:
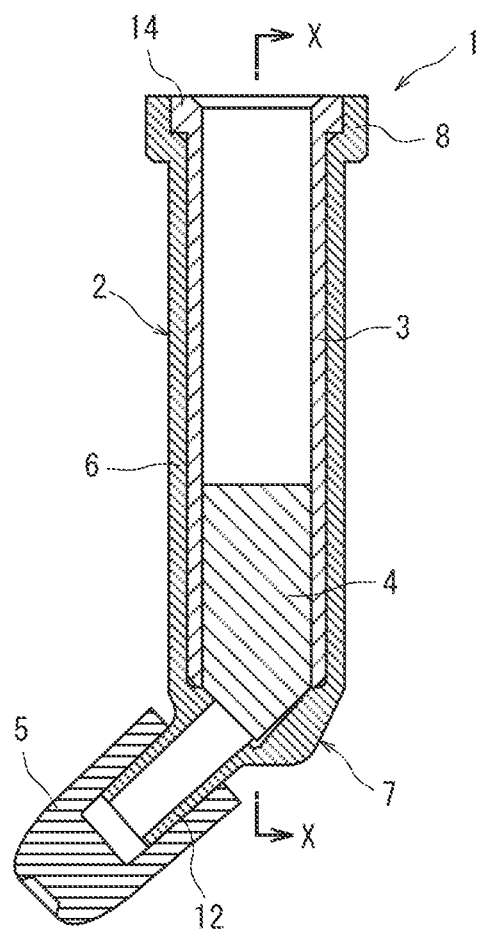
FIG. 1 is a sectional view of an ejection device according to a first embodiment of the invention.
Figure 2:
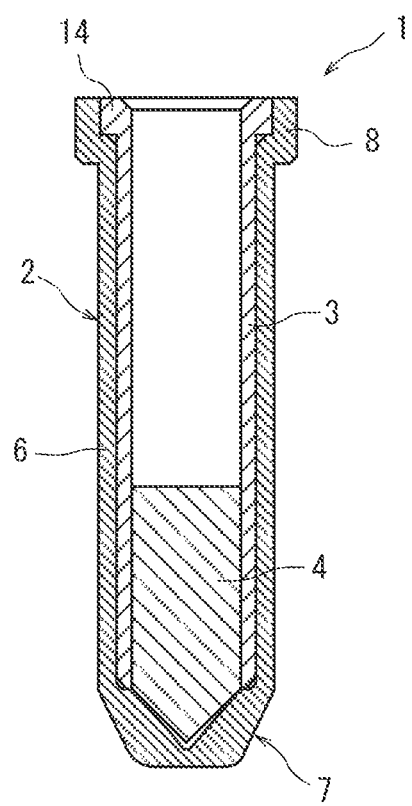
FIG. 2 is a sectional view along the line X-X in FIG. 1.
Figure 3:
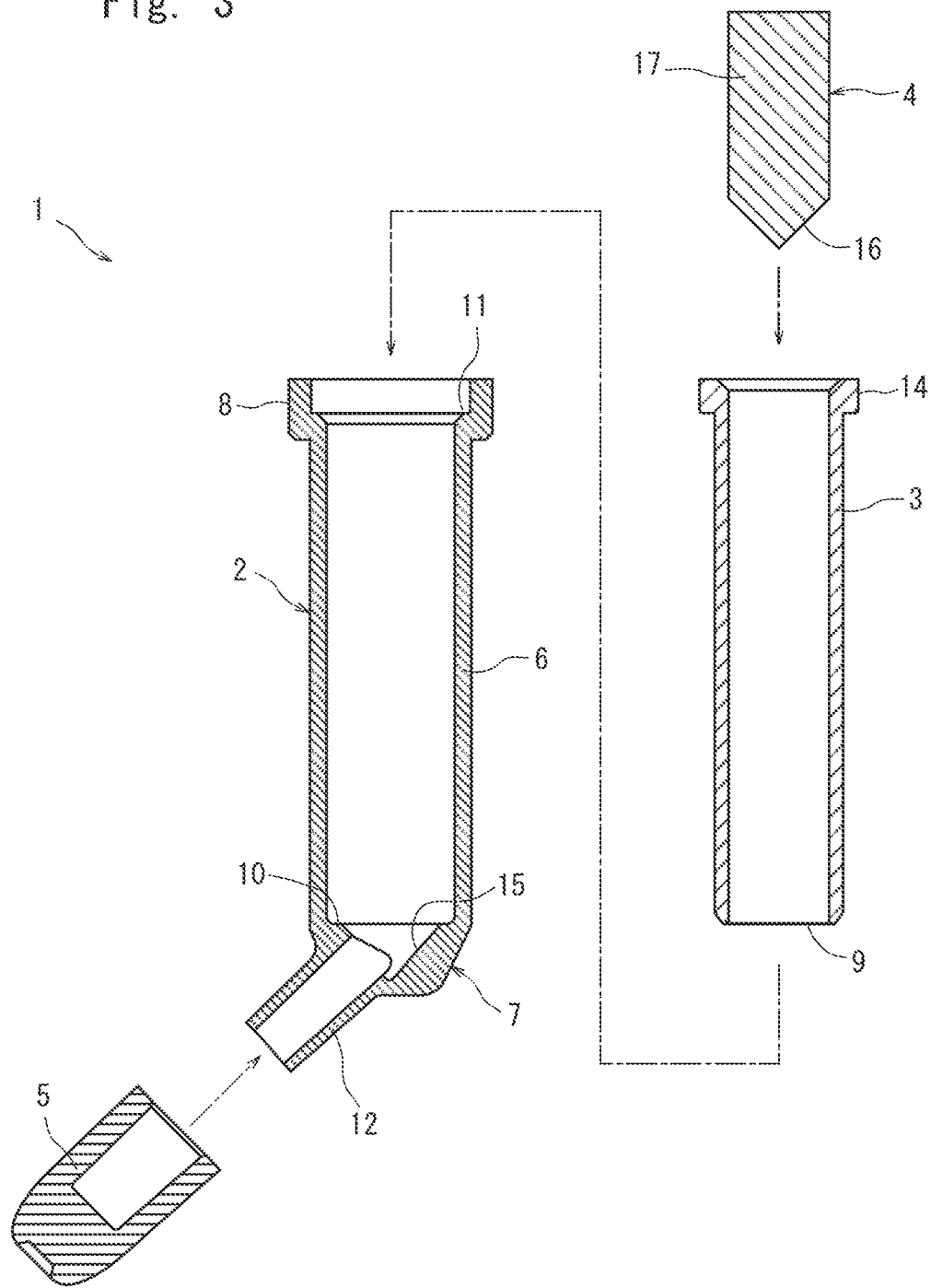
FIG. 3 is a disassembled sectional view of the ejection device of FIG. 1.

FIG. 1 is a sectional view of an ejection device for dental use according to the invention, FIG. 2 is a sectional view along the line X-X in FIG. 1, and FIG. 3 is a disassembled sectional view of the ejection device.

The ejection device 1 is, usually, discarded after it is used one time, and is constituted by a main body 2, a cylindrical member 3, a piston 4 and a cap 5, which are all made of a synthetic resin. The main body 2 is provided with a cylindrical body portion 6, and is forming a discharge portion 7 on the front end side of the body portion and a large diameter portion 8 on the rear end side integrally therewith. The body portion 6 has a circular shape in cross section. On a boundary portion to the discharge portion 7, a stepped portion 10 having a width nearly equal to the thickness of the cylindrical member 3 is formed in the inner periphery surface on the inner side in the radial direction. In the large diameter portion 8 on the rear end side of the body portion 6, a stopper portion 11 is formed forming a step from the inner periphery surface to the outer side in the radial direction.

The discharge portion 7 forms a tapered surface 15 that becomes narrow toward the front end side from the stepped portion 10, and a port of a nozzle 12 is formed in the side portion on the front end side of the tapered surface 15 so as to be communicated with the inner space of the discharge portion 7. The nozzle 12 of a cylindrical shape has the same diameter from the front end thereof up to the rear end thereof. The axis of the nozzle 12 is tilted relative to the axis of the main body by about 45 degrees toward the tilted front end side thereof. A cap 5 is fitted to the front end side of the nozzle 12.

The cylindrical member 3 is contained in the main body 2 in a manner that the inner periphery surface of the main body 2 is in close contact with the outer periphery surface of the cylindrical member 3. A flange portion 14 is formed at the rear end of the cylindrical member 3 so as to protrude outward in the radial direction. The outer shape of the flange portion 14 corresponds to the inner surface shape of the stopper portion 11 of the main body 2. In a state where the cylindrical member 3 is set to the main body 2, therefore, the flange portion 14 is prevented by the stopper portion 11 from moving toward the front end side of the cylindrical member 3. The length from the front end of the cylindrical member 3 to the flange portion 14 is nearly equal to the length from the stopper portion 11 of the main body 2 to the stepped portion 10. The cylindrical member 3 can be contained in the main body 2 without the need of being fixed therein with an adhesive. An opening 9 is formed in the cylindrical member 3 on the front end side thereof. The opening 9 is used as a port for filling the material.

The piston 4 has a conical portion 16 formed at a front end thereof and a pole portion 17 formed on the rear end side thereof. The shape of the conical portion 16 is nearly the same as the inner periphery shape of the tapered surface 15 of the main body 2. As the conical portion 16 comes in contact with the tapered surface 15, the two are overlapped one upon the other as a unitary structure. The outer diameter of the pole portion 17 is the same or nearly the same as the inner diameter of the cylindrical member 3. The outer diameter of the pole portion 17 may be determined by taking the elasticity of the cylindrical member 3 into consideration, and the piston 4 is so formed as to slide along the inner periphery surface of the cylindrical member 3. If closely described, a gap between the outer periphery surface of the piston 4 and the inner periphery surface of the cylindrical member 3 is so formed as to maintain sealing to a degree that permits the air to flow to some extent if a pressure is applied.

The space in the cylindrical member 3 defined by the inner periphery surface of the cylindrical member 3 and the surface of the conical portion 16 of the piston 4 constitutes a filling chamber 24 which is to be filled with the material.

Figure 4:
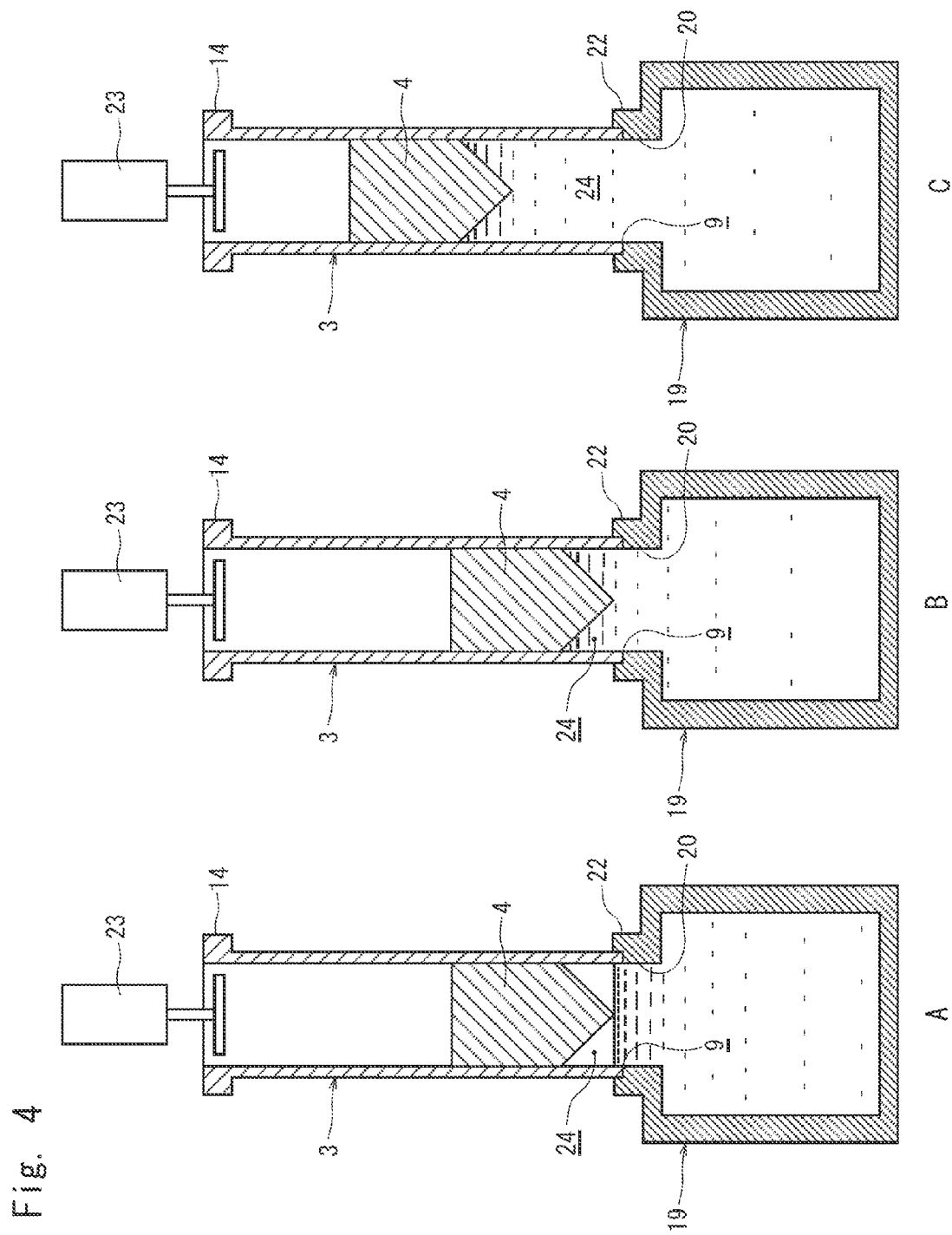
FIG. 4 illustrates a procedure for pouring the material into the ejection device of FIG. 1, wherein A is a sectional view in a state where an end of a cylindrical member is set to an extrusion port of a stock container, B is a sectional view in a state where the material filled in the stock container is pressurized and is poured into a filling chamber and the piston is moving back, and C is a sectional view in a state where the material is further poured and the piston is further moving back.

To pour the material into the ejection device 1, use is made of a stock container 19 though it is not a member that constitutes the ejection device 1. Referring to FIG. 4, the stock container 19 is a container filled with the material that is to be filled, and has an extrusion port 20 formed in one side surface thereof to extrude the material that is to be filled. The extrusion port 20 is provided with a fixing member 22 that is capable of air-tightly setting the one end side of the cylindrical member 3. The stock container 19 is provided with a pressurizing means (not shown) that pressurizes the material to pour it out through the extrusion port 20.

Upon pouring the material into the cylindrical member 3 of the ejection device 1, the piston 4 moves in the filling chamber 24 in the cylindrical member 3 toward the rear side thereof. A position sensor 23 is arranged to detect the rearmost allowable position of the piston 4 in a state where the ejection device 1 is set to the stock container 19.

The position sensor 23 comes in contact with the rear end of the piston 4 and moves back to a predetermined position to thereby detect the rearmost allowable position of the piston 4. Upon detecting the rearmost allowable position of the piston 4 by the position sensor 23, a control unit that is not shown interrupts the pouring of the material into the filling chamber 24 from the stock container 19.

The size and shape of the ejection device 1 may differ variously depending upon the use. It is, however, desired that the ejection device for dental use has an inner diameter of from 2 to 6 mm. In this embodiment, for example, the cylindrical member 3 has an inner diameter of 4.1 mm, a length in the axial direction of 23 mm, and the nozzle 12 has an inner diameter of 1.95 mm; i.e., the nozzle 12 has a sectional area in the radial direction that is very smaller than the sectional area of the cylindrical member 3 in the radial direction.

Next, described below is a procedure for filling the ejection device with the material according to the embodiment.

Referring to FIG. 4A, the ejection device 1 is in a state of being separated from the main body 2. First, the piston 4 is set in the inner circumference of the cylindrical member 3 on the front end side thereof. In this case, the conical portion 16 of the piston 4 is arranged facing the opening 9. Next, the opening 9 at the end of the cylindrical member 3 is set to the extrusion port 20 of the stock container 19. On other words, the opening 9 is attached to the fixing member 22. With the cylindrical member 3 being fixed to the stock container 19, the material filled in the stock container 19 is pressurized by a pressurizing means that is not shown.

Here, examples of the viscous material that is filled for dental use may include a dental cement, a indirect dental restorative material and a dental restorative filling material.

Referring to FIG. 4B, upon being pressurized, the material filled in the stock container 19 is poured into the opening 9 of the cylindrical member 3 from the extrusion port 20. The inner diameter of the cylindrical member 3 is of such a size that permits the piston 4 to be loosely fitted therein. Therefore, the inner periphery surface of the cylindrical member 3 and the outer periphery surface of the piston 4 are maintaining such an air-tightness that the air can be released with a suitable degree of load. With the air being released, the material can be poured into the filling chamber 24 without forming voids. The material that is filled does not escape due to its viscosity.

Referring to FIG. 4C, upon pouring the material into the filling chamber 24, the piston 4 moves back being pushed by the material that is filled. The inner diameter of the opening 9 of the cylindrical member 3 (inner diameter of the filling chamber 24) is larger than the inner diameter of the nozzle 12. Upon increasing the inner diameter of the opening 9, a high pressure is not applied to the material that is filled despite the material is poured into the filling chamber 24 through the extrusion port 20 by applying a pressure thereto by the pressurizing means that is not shown of the stock container 19. This eliminates the phenomenon in that the material that is filled separates into liquid components and solid components or the problem of curing. Therefore, the present invention exhibits the effect that becomes conspicuous as the inner diameter of the nozzle 12 becomes smaller than the inner diameter of the opening 9. Further, the pressure for extruding the material increases with an increase in the viscosity of the material, and further improved effect is exhibited.

Figure 5:
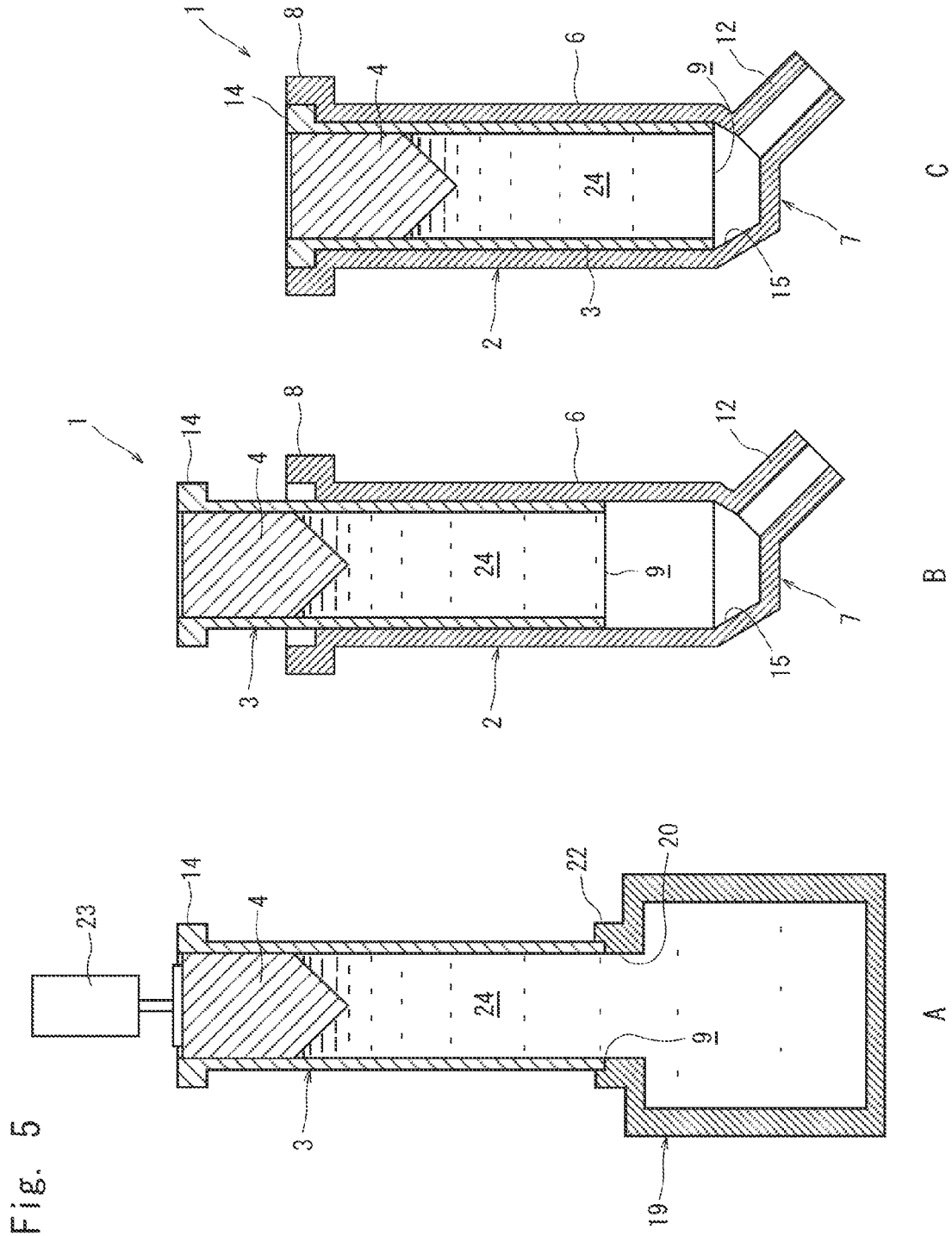
FIG. 5 A is a sectional view in a state where the filling chamber is filled with the material, B is a sectional view in a state where the cylindrical member is inserted in the main body, and C is a sectional view in a state where the cylindrical member is contained in the main body.

Referring to FIG. 5A, the material is poured into the filling chamber 24, the piston 4 moves back to come in contact with the position sensor 23, and a detector portion of the position sensor 23 moves back by a predetermined amount. As the detector portion moves back, a control portion (not shown) electrically connected to the position sensor 23 decides that the piston 4 has reached the rearmost allowable position, whereby the material is no more poured and the filling chamber 24 has now been filled with a predetermined amount of the material. As shown in the states of FIG. 4A and FIG. 4B, the air on the front end side of the piston 4 is released and the amount of the material that is filled is monitored by the position sensor 23 making it possible to feed the material in a correct amount to the filling chamber 24.

Referring to FIG. 5B, after the filling chamber 24 has been filled with the material in a predetermined amount, the cylindrical member 3 is removed from the stock container 19 and is inserted in the main body 2 so as to be contained therein. The flange portion 14 has been formed at the rear end portion of the cylindrical member 3. Referring to FIG. 5C, the flange portion 14 is restricted from moving due to the stopper portion 11 of the main body 2 and, therefore, the cylindrical member 3 contained in the main body 2 is positioned therein.

Here, if the material that is filled is of a nature that may be deteriorated by the air remaining in the filling chamber 24 and in the nozzle 12, then the piston 4 may be pushed to expel the remaining air by the material that is filled and, thereafter, the cap 5 may be fitted to the nozzle 12.

At the time of use, the ejection device 1 is set to an extruder called applicator such as gun. Upon pulling the trigger of the applicator, the piston 4 in the ejection device 1 is pushed by a push mechanism of the applicator, and the material that is filled is ejected.

In this embodiment as described above, the material to be filled can be poured into the filling chamber 24 with a small pressurizing force. Therefore, the filling chamber 24 is filled with the material without causing a decrease in the quality thereof.

Figure 6:
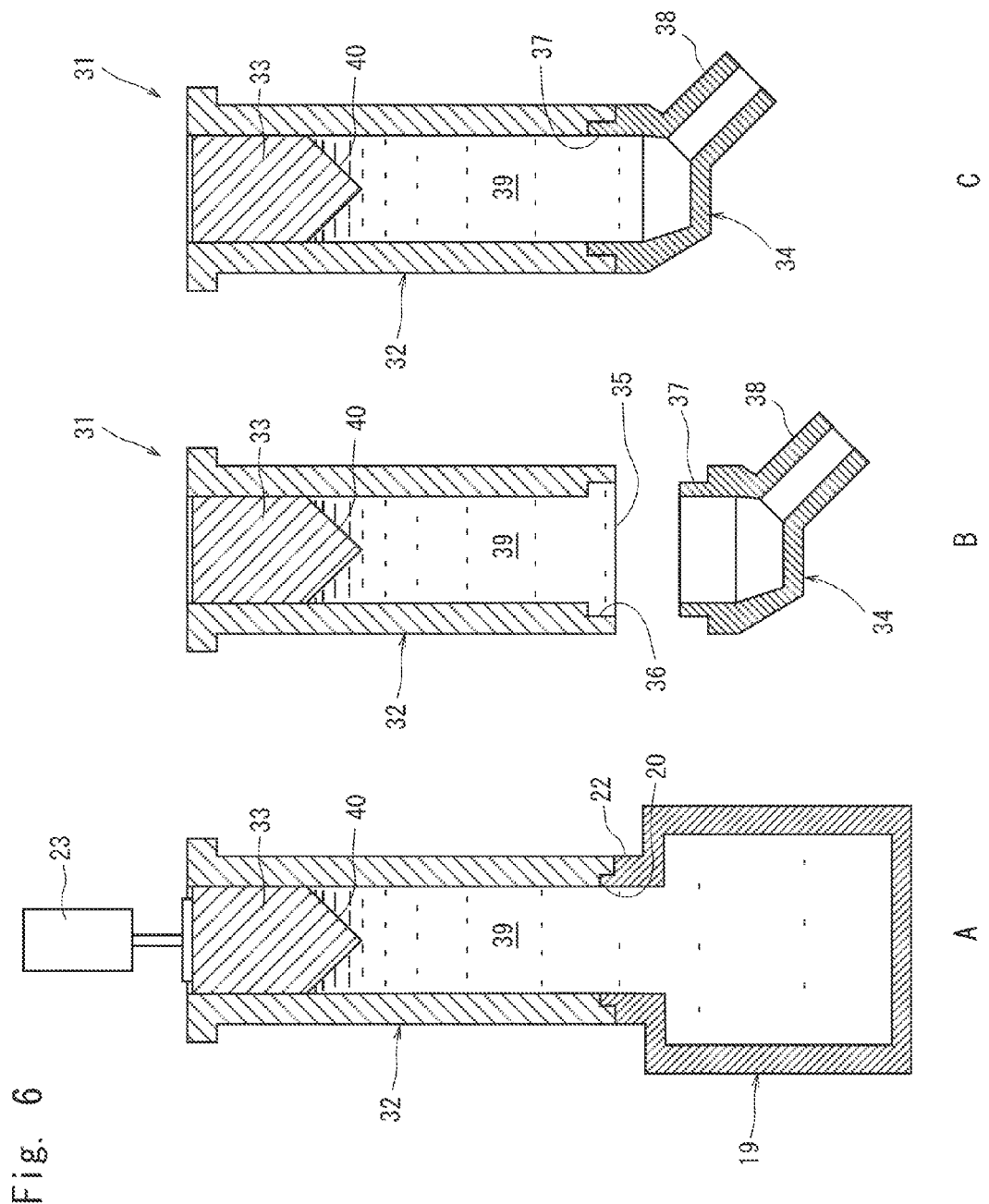
FIG. 6 shows the ejection device according to a second embodiment of the invention, wherein A illustrates a state where the material is poured from the stock container into the filling chamber, B is a sectional view in a state before the discharge portion is fitted to the filling chamber, and C is a sectional view in a state of where the discharge portion is fitted to the filling chamber.

The ejection device according to a second embodiment of the invention and a method of filling the ejection device with the material will be described next with reference to FIG. 6.

Referring to FIG. 6B, the ejection device 31 is constituted by a cylindrical member 32, a piston 33 and a discharge portion 34, which are all made of a synthetic resin.

In the above first embodiment, the main body 2 is provided, and the cylindrical member 3 is contained in the main body 2. In this embodiment, however, the main body 2 is omitted. In the above embodiment, further, the discharge portion 7 is formed integrally with the main body 2. In this embodiment, however, the discharge portion 34 is joined directly to the cylindrical member 32 making a difference from the above embodiment.

Referring to FIG. 6B, an annular groove 36 is formed in the inner periphery surface of an opening 35 at one end of the cylindrical member 32. Being corresponded to the annular groove 36, the discharge portion 34 forming a nozzle 38 has an annular protruded portion 37 formed on the edge of an opening thereof. With the annular protruded portion 37 being fitted to the annular groove 36, the cylindrical member 32 and the discharge portion 34 are air-tightly and integrally formed together. They may be joined together by melt-adhesion (heat, ultrasonic waves, etc.), by using an adhesive or by screw though dependent upon the kind of the material that is to be filled.

The piston 33 is arranged in the cylindrical member 32. The space in the cylindrical member 32 defined by the inner periphery surface of the cylindrical member 32 and the surface of the conical portion 40 of the piston 33, serves as the filling chamber 39 to be filled with the material.

The stock container 19 and the position sensor 23 are the same as those described in the first embodiment but are not described here again, though the fixing member 22 has a shape a little different from the above one.

As for a procedure for filling the ejection device 31 with the material according to this embodiment, the opening 35 at one end (front end side) of the cylindrical member 32 may be fixed to the stock container 19 as shown in FIG. 6A. The procedure in other respects is the same as that of the above first embodiment (FIGS. 4A to 4C, FIG. 5A).

After the material has been poured into the filling chamber 39 of the ejection device 31, the annular protruded portion 37 of the discharge portion 34 is fitted to the annular groove 36 formed in the opening 35 of the cylindrical member 32 to complete the ejection device 31.

As described above, the discharge portion 34 may be directly coupled to the cylindrical member 32. Employment of this constitution, too, makes it possible to prevent the application of a high pressure on the material filled in the filling chamber 39 in the same manner as in the above embodiment. Besides, the number of parts can be decreased. This eliminates the phenomenon in that the material that is filled separates into liquid components and solid components and the problem of curing. It is, further, made possible to fill the filling chamber 39 with the material in a correct amount.

Figure 7:
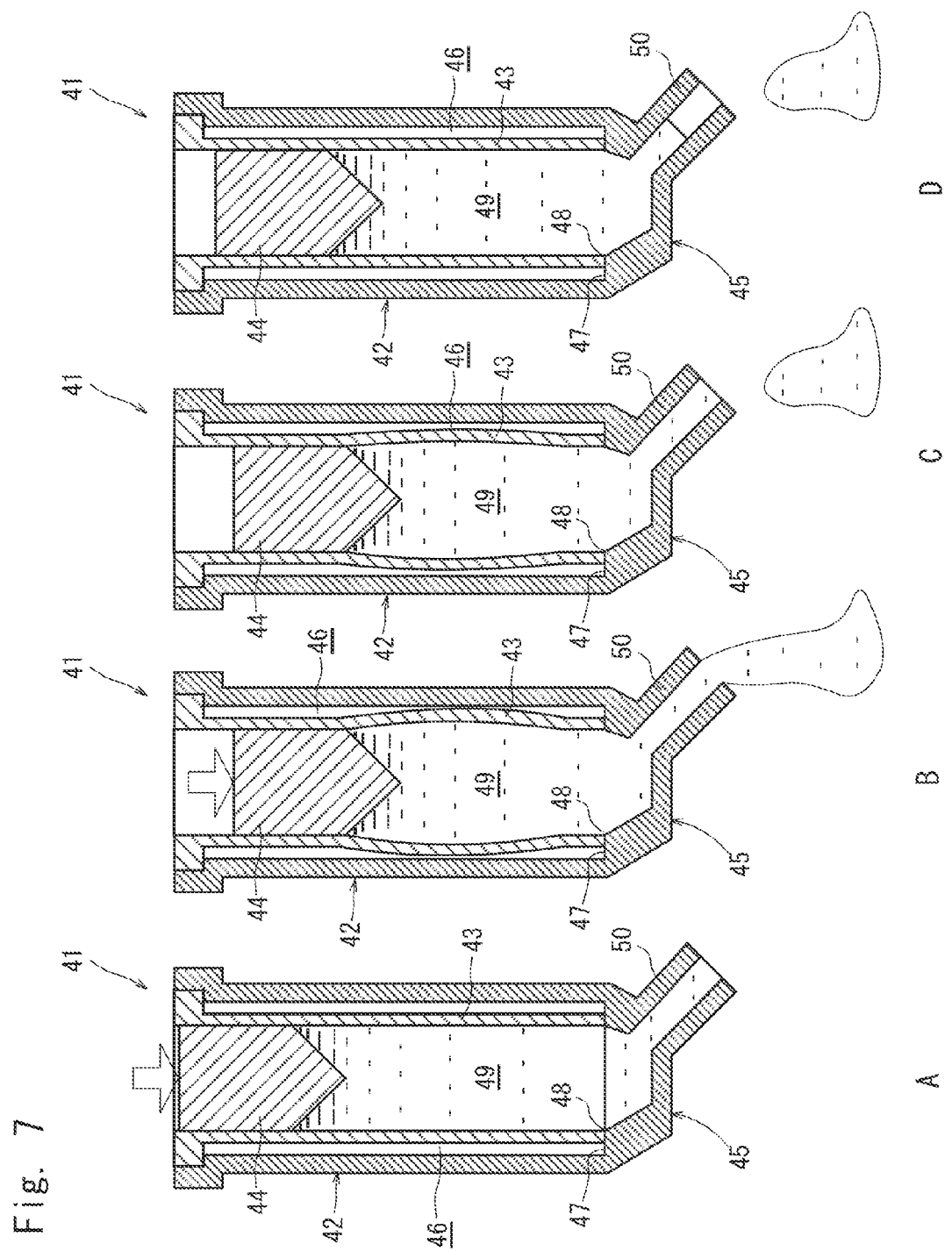
FIG. 7 is a view illustrating the operation of the ejection device according to a third embodiment of the invention, wherein A is a sectional view in a state where the filling chamber is filled with the material, B is a sectional view in a state where the material that is filled is extruded by the piston, C is a sectional view of just before discontinuing the extrusion of the material that is filled, and D is a sectional view of just after having discontinued the extrusion of the material that is filled.

The ejection device according to a third embodiment of the invention and a method of filling the ejection device with the material will be described next with reference to FIG. 7.

Referring to FIG. 7A, the ejection device 41 is constituted by a main body 42, a cylindrical member 43 and a piston 44, which are all made of a synthetic resin.

This embodiment is substantially different from the above first embodiment with respect to that a gap 46 is formed between the inner periphery surface of the main body 42 and the inner periphery surface of the cylindrical member 43 and that the cylindrical member 43 is made of a material that exhibits elasticity if the internal pressure exceeds a predetermined value.

In other words, a discharge portion 45 is formed integrally with the main body 42, and the cylindrical member 43 that forms the filling chamber 49 is separate from the main body 42 and the discharge portion 45. A stepped portion 47 is formed at the end of the cylindrical member 43 and at the boundary portion between the main body 42 and the discharge portion 45, the stepped portion 47 extending inward in the radial direction from the inner periphery surface of the main body 42. In a state where the cylindrical member 43 is contained in the main body 42, the opening 48 on the front end side of the cylindrical member 43 comes in contact with the stepped portion 47.

As described above, a gap is formed between the inner circumference of the main body 42 and the outer periphery surface of the cylindrical member 43. The cylindrical member 43 is made of an elastic material while the main body 42 is made of a synthetic resin material having a relatively small elasticity.

The procedure for filling the ejection device 41 of this embodiment with the material is the same as the one described in the above first embodiment (FIGS. 4A to 4C, FIG. 5A). That is, the material is poured into the opening 48 of the cylindrical member 43 by using the stock container 19.

After the material has been poured into the filling chamber 49 of the ejection device 41, the cylindrical member 43 filled with the material is contained in the main body 42 as shown in FIG. 7A.

Employment of this structure, too, prevents a high pressure from being applied onto the material filled in the filling chamber 49 like in the above first embodiment. This eliminates the phenomenon in that the material that is filled separates into liquid components and solid components and the problem of curing. It is, further, made possible to fill the filling chamber 49 with the material in a correct amount.

The ejection device 41 of this embodiment, further, exhibits the following effects in addition to the effects of the above first embodiment.

To release the air present in the discharge portion 45 as shown in FIG. 7A, the piston 44 is moved forward as shown in FIG. 7B to extrude the material filled in the filling chamber 49. If the filled material is ejected from a nozzle 50, pushing the piston 44 is halted as shown in FIG. 7C. Then, the material fills up to the front end portion of the nozzle 50 as shown in FIG. 7C. This is not limited to the case of releasing the air only; i.e., the material is filling up to the front end portion of the nozzle 50 even when the ejection device 41 is used being divided into a plurality of times, e.g., is used in the second time.

However, the material may often remain on the outer side of the port of the nozzle 50, may adhere to the front end portion of the nozzle 50, and may hang down from an undesired portion. If the air is contained in the filling chamber 49, the material having a low viscosity may often spout out of the nozzle 50 due to a change in the temperature. In particular, when the ejection device 41 being stored in a refrigerating chamber is taken out, the material may often undesirably spout out of the nozzle 50 due to the expansion of the air caused by a change in the temperature.

In this embodiment, if the internal pressure is elevated in the cylindrical member 43, the periphery wall of the cylindrical member 43 expands outward upon receiving the internal pressure as shown in FIG. 7B and in this state, the material that is filled is ejected. Then, as shown in FIG. 7C, the material is ejected to a desired place and the piston is no more pushed. Then, as shown in FIG. 7D, the periphery wall of the cylindrical member 43 returns back to the initial state overcoming the internal pressure of the material. Here, the volume of the cylindrical member 43 decreases from its expanded state as the cylindrical member 43 returns from the state shown in FIG. 7C back to the state shown in FIG. 7D. Accordingly, the material present in the opening of the nozzle 50 is pulled back into the nozzle 50 (see FIG. 7D). Accordingly, the material that is left on the outer side of the port of the nozzle 50, too, is pulled back and is prevented from adhering to the end portion of the nozzle 50. Moreover, even if the air is contained in the filling chamber 49, the material is prevented from spouting out despite of a change in the temperature. Specifically, the ejection device 41 of this embodiment has an advantage in that the air present in the gap between the main body 42 and the cylindrical member 43 exhibits heat-insulating effect.

Though not specifically referred to concerning the material of the cylindrical member and the size of the gap, the cylindrical member 43 should have elasticity so as to expand depending on the internal pressure of the filled material and should be so adjusted that the material that is filled returns back to the side of the filling chamber 49. The wall of the main body 42 may be utilized as a stopper to prevent the cylindrical member 43 from expanding in excess of a predetermined degree.

Figure 8:
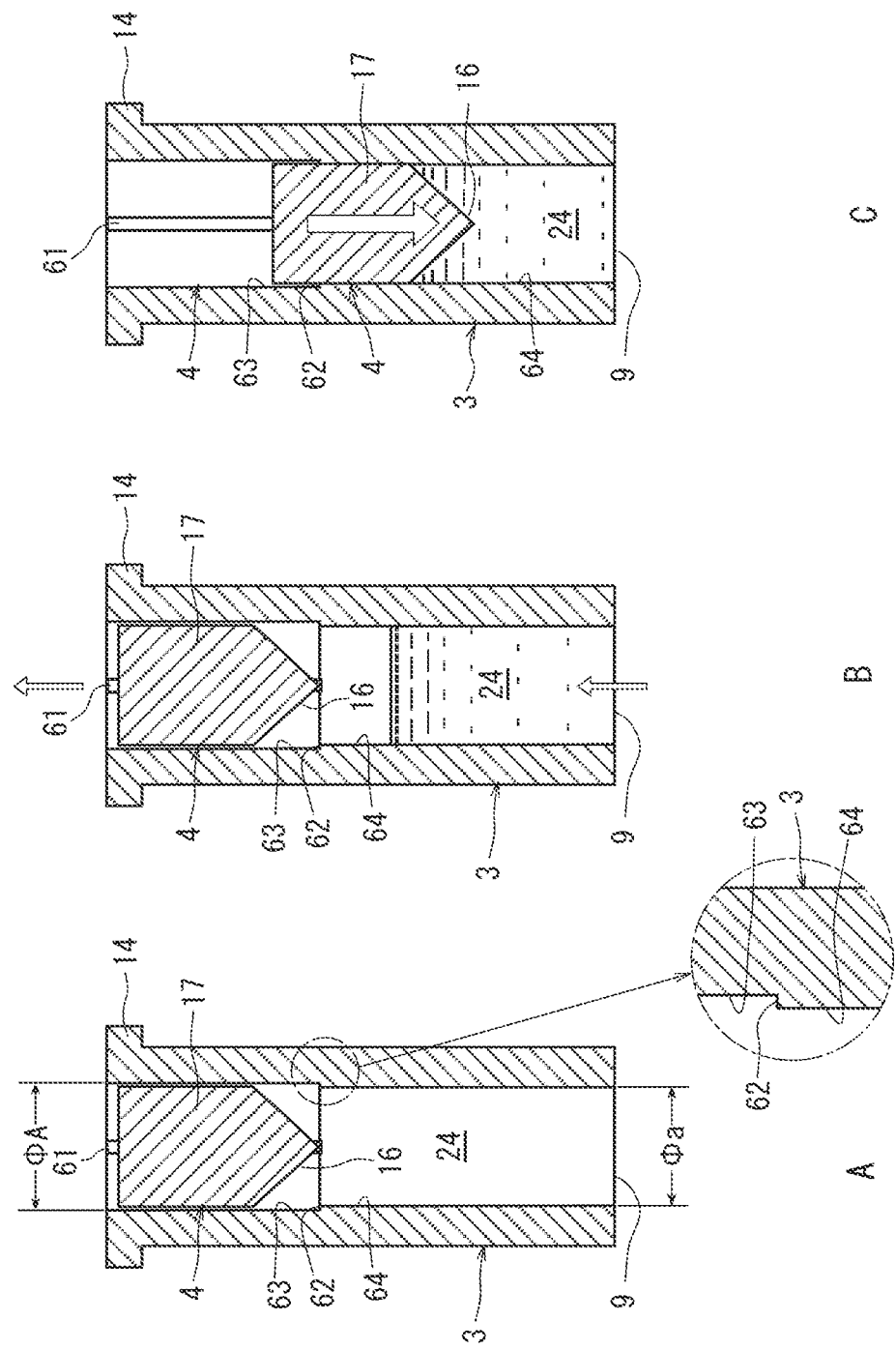
FIG. 8 shows the ejection device according to a fourth embodiment of the invention, wherein A is a sectional view of the cylindrical member and the initial position of the piston at the time of pouring the material into the ejection device, B is a sectional view in a state where the material is poured half, and C is a sectional view of when the material that is filled is poured out.

The ejection device according to a fourth embodiment of the invention and a method of filling the ejection device with the material will be described next with reference to FIG. 8. The cylindrical member of this embodiment is different in shape from the cylindrical member 3 of the first embodiment, but is denoted by the same reference numeral for easy description.

The ejection device 1 of this embodiment is constituted by the main body 2 (see FIG. 1), cylindrical member 3, piston 4 and cap 5 (see FIG. 1). The main body 2 and the cap 5 are the same ones as those used in the first embodiment and, therefore, reference is also made to FIG. 1.

The piston 4 is contained in the cylindrical member 3 of a circular shape in cross section that contains the material therein, the piston 4 sliding along the inner periphery surface of the cylindrical member 3. The filling chamber 24 is formed on the side in front of the piston 4. The opening 9 is formed in one end of the filling chamber 24 (cylindrical member 3) to receive the material that is to be filled.

A linear groove 61 is formed in the inner periphery surface of the cylindrical member 3 extending from the rear side (other end side) of the cylindrical member to the front side (one end side) thereof. The groove 61 is of a triangular shape in cross section, the width (base of the triangle) thereof being, preferably, from 0.3% to 3% and, in this embodiment, being 0.8% of the inner periphery length of the cylindrical member 3. The depth of the groove 61 (height of the triangle) is, preferably, from 10 to 40% and, in this embodiment, 18% of the thickness of the periphery wall of the cylindrical member 3. The sectional area of the groove 61 is, preferably, not less than 0.01% and, specifically, not less than 0.02% and, in this embodiment, not less than 0.04% of the inner spatial sectional area of the cylindrical member 3 (excluding the sectional area of the groove 61). The grooves 61 may be formed in a plural number in the inner periphery surface of the cylindrical member 3 maintaining a predetermined distance.

When the piston 4 is at its retreated position, the groove 61 must be extending up to the side of the filling chamber 24 exceeding a portion where the outer periphery surface of the pole portion 17 of the piston 4 is in contact with the inner periphery surface of the cylindrical member 3. On other words, when the piston 4 is at its retreated position, the filling chamber 24 and the cylindrical member 3 are communicated with each other on the other end side thereof through the groove 61.

A step 62 is formed in the inner periphery surface of the cylindrical member 3 to protrude inward in the radial direction being corresponded nearly to an end portion of the groove 61 on the side of the filling chamber 24. From the step 62 to the rear end side of the cylindrical member 3, therefore, the inner diameter is large though by only a small amount, forming an expanded diameter portion 63 in which the piston can be inserted in a loosely fitted state. The cylindrical member 3 has an inner diameter from the step 62 up to the opening 9, that is smaller than that of the rear end side, and is forming a contracted diameter portion 64 in which the piston can be inserted in a tightly fitted state.

The end portion of the groove 61 may be so formed as to protrude toward the front end side of the cylindrical member 3 beyond the step 62 by about 2 mm. In this embodiment, the end portion is formed protruding by 1 mm. It is, further, desired that with the step 62 as a boundary, the inner diameter a of the contracted diameter portion 64 on the front end side is smaller by 1 to 6% than the outer diameter of the pole portion 17 of the piston 4 so that the piston 4 is inserted in the contracted diameter portion 64 in a tightly fitted state. In this embodiment, the inner diameter a is smaller by 2% and is, concretely, 4.1 mm. It is desired that the inner diameter A of the expanded diameter portion 63 on the rear end side is equal to, or larger by 0 to 2% than, the outer diameter of the pole portion 17 of the piston 4 so that the piston 4 is inserted in the expanded diameter portion 63 in a loosely fitted state. In this embodiment, the inner diameter A and the outer diameter of the pole portion 17 are of the same size which is, concretely, 4.2 mm. Therefore, the step 62 in this embodiment has a width of 0.05 mm.

The cylindrical member is contained in the main body 2 (FIG. 1) in a manner that the inner periphery surface of the main body 2 is in close contact with the outer periphery surface of the cylindrical member 3.

Like in the above first embodiment, the piston 4 is provided with the conical portion 16 at its end and with the pole portion 17 on the rear end side. The piston 4 is so formed as to slide along the inner periphery surface of the cylindrical member 3.

Next, described below is a procedure for filling the ejection device with the material according to this embodiment.

This embodiment is used specifically for filling the filling chamber 24 with a lowly viscous material. This is because if the same cylindrical member as that of the above first embodiment is used for filling a lowly viscous material, then the material leaks through between the cylindrical member 3 and the piston 4 when it is being filled or being ejected, and bubbles mix into the material that is filled. The material to be filled in this embodiment has a viscosity of from 10 to 2000 poises and, preferably, from 50 to 1000 poises.

To pour the material that is to be filled, the piston 4 is disposed at its retreated position as shown in FIG. 8A. That is, the piston 4 is disposed at a position at which the material is filled in a suitable amount or at a position slightly in front of the position of suitable amount. This position is in the expanded diameter portion 63 of the cylindrical member 3. As described above, the inner diameter of the cylindrical member 3 is smaller in the contracted diameter portion 64 than the outer diameter of the pole portion 17 of the piston 4. Even when the material is poured by vertically erecting the cylindrical member 3, therefore, the outer periphery wall of the piston 4 disposed in the expanded diameter portion 63 of the cylindrical member 3 does not enter to the front end side (to the side of the contracted diameter portion 64) beyond the step 62.

Next, upon pressurizing the material in the stock container 19 (see FIG. 4), the material is poured into the opening 9 of the cylindrical member 3. As the material is poured into the filling chamber 24 as shown in FIG. 8B, the groove 61 in the filling chamber 24 serves as an air release passage and the air is released from the filling chamber 24. The piston 4 is positioned in the expanded diameter portion 63 of the cylindrical member 3. Therefore, the air in the filling chamber 24 is released through the gap between the inner periphery surface of the cylindrical member and the outer periphery surface of the piston, too. After the air is released, the pressure produced by the stock container 19 and applied to the material that is filled is not so large as to entrap the air, and the bubbles are prevented from generating.

Here, if the piston 4 is arranged at the front end position from the first time as in the above first embodiment, it is not easy to move back or to smoothly operate the piston 4 since the outer diameter of the piston 4 is larger than the inner diameter of the contracted diameter portion 64 permitting the air to remain. Besides, the air pressure is applied to the material that is filled to generate bubbles. If the filling chamber 24 is filled with the material of a suitable amount, the position sensor 23 (FIG. 4) detects it to discontinue the pouring.

At the time of ejection of the ejection device 1, the piston 4 moves forward to apply an internal pressure to the filling chamber 24. However, since the groove 61 has a small sectional area, the material that is viscous to some extent does not escape through the groove 61 unlike the air. The piston 4 is at its retreated position. Upon being moved forward even by a small distance, the pole portion 17 of the piston 4 arrives at the contracted diameter portion 64. Thus, the pole portion 17 closes the groove 61. Besides, since the outer diameter of the pole portion 17 is larger than the inner diameter of the contracted diameter portion 64, the outer periphery surface of the piston 4 comes in close contact with the inner periphery surface of the cylindrical member 3, and the material that is filled is effectively prevented from leaking. Since the air has been released from the filling chamber 24, no bubble generates even if a high pressure is applied to the material that is filled.

Further, the piston 4 that has moved forward hits the step 62. Here, however, the piston 4 has a conical shape at its front end and is allowed to smoothly move forward. If the piston is inserted in the contracted diameter portion at the time of pouring the material, a large load is exerted on the material in addition to the pressure of pouring the material and is not desirable. When the piston moves forward at the time of pouring out the material, however, the load applied to the material is not as large as that of when the material is poured in, and the piston is allowed to move forward smoothly in the contracted diameter portion 64. Even when the material that is filled has a high viscosity, furthermore, the amount that is poured out can be minutely controlled due to a suitable degree of load of when the piston moves forward.

The shape of the step 62 may be a conical (tapered) surface of which the diameter contracts toward the front side. When the piston 4 is formed in the shape of a pole, in particular, catching is effectively prevented.

Here, as a further embodiment, it was attempted to pour the material through the opening 9 by using a cylindrical member 3 forming the groove 61 only but without forming the step 62, and the air could be released. Further, when the piston 4 was pushed at the time of pouring the material from the ejection device 1, the material leaked slightly through the groove 61 and between the pole portion 17 of the piston and the cylindrical member 3.

It was further attempted to pour the material through the opening 9 by using the cylindrical member formed in the same size as the inner diameter of the expanded diameter portion 63 without forming the groove 61. It was confirmed that the air remained in small amounts in the filling chamber 24 with the piston 4 being at its retreated position.

In these embodiments, the material having a low viscosity yielded the above results. If the material has an intermediate viscosity, the air only can be released through the groove 61 without, however, permitting the material to leak even by using the cylindrical member 3 forming the groove 61 only if the size of the groove 61 is suitably selected. Further, even by using the cylindrical member 3 forming the step 62, the air only can be released through between the pole portion 17 of the piston 4 and the inner periphery surface of the cylindrical member 3 without, however, releasing the material if the inner diameter of the inner surface of the cylindrical member 3 is adjusted.

Upon forming the groove 61 and the step 62, however, it is allowed to more distinctly exhibit the effect of releasing the air only from the filling chamber 24 while preventing the leakage of the material that is filled, and to easily attain the adjustment.

Though the invention was described above in detail based on the embodiments with reference to the accompanying drawings, it should be noted that the invention is in no way limited to the above embodiments only but can be modified or changed in various other forms without departing from the scope of the invention.

For example, in the above third embodiment, a gap was formed between the main body 42 and the cylindrical member 43, and elasticity was imparted to the cylindrical member 43 to return the material back to the inner side of the nozzle 50. However, in the above second embodiment, too, the cylindrical member 32 may be made of an elastic material so as to expand in the outer periphery direction when the material that is filled is pushed by the piston 33. In this case, however, the stopper effect is not obtained by the main body, and the heat-insulating effect due to the formation of gap is not obtained, either.

The groove 61 and step 62 formed in the cylindrical member of the fourth embodiment of the invention were described by using the first embodiment, which, however, can also be applied to the second embodiment and to the third embodiment. In the third embodiment, however, the elasticity is so large that the conditions for the groove and step may become different.

Further, though the groove 61 was formed in a triangular shape in cross section, the shape may be suitably changed into a square or semicircular shape, too.

DESCRIPTION OF REFERENCE NUMERALS 1, 31, 41 ejection devices
2, 42 main bodies
3, 43 cylindrical members
4, 33, 44 pistons
7, 34, 45 discharge portions
9 opening (filling port)
12, 38, 50 nozzles
19 stock container
20 extrusion port
22 fixing member
23 position sensor
24, 39, 49 filling chambers
46 gap
61 groove
62 step
63 expanded diameter portion
64 contracted diameter portion

The invention claimed is:

1. An ejection device comprising:
a filling chamber formed in a cylindrical member for containing a material to be filled;
a discharge portion having a discharge nozzle for pouring out the filled material to the exterior;
a piston that pushes said filled material toward a front end side of said filling chamber to discharge the filled material through said discharge nozzle; and
a main body for removably containing the cylindrical member that is forming said filling chamber, said main body and said discharge portion being integrally formed together, wherein
said discharge portion is formed separately from said cylindrical member and in a manner to be fitted to an opening on one end side of said cylindrical member,
said opening is formed in a manner to be connected to an extrusion port of a stock container which pours said material to be filled into said filling chamber as a filling port for filling said material to be filled,
a gap between an outer periphery surface of the piston and an inner periphery surface of the cylindrical member is so formed as to maintain sealing to a degree that permits air to be released without letting the material to be filled escape, and
after said discharge portion is arranged in said opening on the one end side and said material to be filled is poured into said filling chamber through said filling port while pushing the piston back with said material to be filled extruded from said filling chamber, said discharge portion is coupled to said opening of said cylindrical member.

2. The ejection device according to claim 1, wherein said filling chamber is made of an elastic member so that the volume of said cylindrical member elastically increases when said piston is pushed, a gap is formed between said main body and said cylindrical member, and the volume of said filling chamber decreases when said piston is no longer pushed.

3. The ejection device according to claim 1, wherein a groove is formed in the inner periphery surface of said cylindrical member, said groove being formed from other end side of the cylindrical member up to the interior of the filing chamber with said piston at its retreated position.

4. The ejection device according to claim 3, wherein a step is formed in the inner periphery surface of said cylindrical member being corresponded to an end portion of said groove on the side of the filling chamber, the portion from said step to the opening on one end side of said filling chamber being a contracted inner diameter portion in which said piston is inserted in a tightly fitted state, and a portion from said step to the opening on the other end side of said filling chamber being an expanded inner diameter portion in which said piston is inserted in a loosely fitted state.

5. The ejection device according to claim 2, wherein a groove is formed in the inner periphery surface of said cylindrical member, said groove being formed from other end side of the cylindrical member up to the interior of the filing chamber with said piston at its retreated position.

6. The ejection device according to claim 5, wherein a step is formed in the inner periphery surface of said cylindrical member being corresponded to an end portion of said groove on the side of the filling chamber, the portion from said step to the opening on one end side of said filling chamber being a contracted inner diameter portion in which said piston is inserted in a tightly fitted state, and a portion from said step to the opening on the other end side of said filling chamber being an expanded inner diameter portion in which said piston is inserted in a loosely fitted state.

7. A method of filling an ejection device with a material by filling a filling chamber of the ejection device of claim 1 with a material that is introduced with pressure from a stock container filled with the material through an extrusion port formed in the stock container, comprising:
- a step of setting the extrusion port by connecting the opening on one end side of said filling chamber to the extrusion port of said stock container, and setting the piston on the side of said opening;
- a step of pressurizing the material filled in said stock container;
- a step of filling said filling chamber with the material while pushing said piston backward by the material extruded through said extrusion port in said pressurizing step;
- and a step of coupling the discharge portion equipped with a nozzle for pouring out the material to the opening on one end side of said filling chamber after the filling chamber has been filled with the material.

8. A method of filling an ejection device with a material by filling a filling chamber of the ejection device of claim 3 with a material that is introduced with pressure from a stock container filled with the material through an extrusion port formed in said stock container, comprising:
- a step of setting the extrusion port by connecting the opening on one end side of said filling chamber to the extrusion port of said stock container, and setting the piston at its retreated position;
- a step of pressurizing the material filled in said stock container;
- a step of filling said filling chamber with the material while releasing the air in said filling chamber through the groove formed in the inner periphery surface of the cylindrical member in said pressurizing step; and
- a step of coupling the discharge portion equipped with a nozzle for pouring out the material to the opening on one end side of said filling chamber after said filling chamber has been filled with the material.

9. A method of filling an ejection device with a material by filling a filling chamber of the ejection device of claim 4 with a material that is introduced with pressure from a stock container filled with the material through an extrusion port formed in said stock container, comprising:
- a step of setting the extrusion port by connecting the opening on one end side of said filling chamber to the extrusion port of said stock container, and setting the piston at its retreated position;
- a step of pressurizing the material filled in said stock container;
- a step of filling said filling chamber with the material while releasing the air in said filling chamber through the groove formed in the inner periphery surface of the cylindrical member in said pressurizing step; and
- a step of coupling the discharge portion equipped with a nozzle for pouring out the material to the opening on one end side of said filling chamber after said filling chamber has been filled with the material,
wherein in said step of filling, the filling chamber of the ejection device of claim 4 is filled with the material while also releasing the air in said filling chamber through a gap between the inner periphery surface of the cylindrical portion in the expanded diameter portion of the cylindrical member and the outer periphery surface of said piston.

10. A method of filling an ejection device with a material by filling a filling chamber of the ejection device of claim 2 with a material that is introduced with pressure from a stock container filled with the material through an extrusion port formed in the stock container, comprising:
- a step of setting the extrusion port by connecting the opening on one end side of said filling chamber to the extrusion port of said stock container, and setting the piston on the side of said opening;
- a step of pressurizing the material filled in said stock container;
- a step of filling said filling chamber with the material while pushing said piston backward by the material extruded through said extrusion port in said pressurizing step; and
- a step of coupling the discharge portion equipped with a nozzle for pouring out the material to the opening on one end side of said filling chamber after the filling chamber has been filled with the material.

11. A method of filling an ejection device with a material by filling a filling chamber of the ejection device of claim 5 with a material that is introduced with pressure from a stock container filled with the material through an extrusion port formed in said stock container, comprising:
- a step of setting the extrusion port by connecting the opening on one end side of said filling chamber to the extrusion port of said stock container, and setting the piston at its retreated position;
- a step of pressurizing the material filled in said stock container;
- a step of filling said filling chamber with the material while releasing the air in said filling chamber through the groove formed in the inner periphery surface of the cylindrical member in said pressurizing step; and
- a step of coupling the discharge portion equipped with a nozzle for pouring out the material to the opening on one end side of said filling chamber after said filling chamber has been filled with the material.

\* \* \* \* \*